US012048713B2

(12) United States Patent
Shyam et al.

(10) Patent No.: US 12,048,713 B2
(45) Date of Patent: Jul. 30, 2024

(54) PHARMACEUTICAL COMPOSITION FOR REDUCING PROTEIN BOUND UREMIC TOXINS

(71) Applicant: Frimline Private Limited, Ahmedabad (IN)

(72) Inventors: Ankit Shyam, Ahmedabad (IN); Alpesh Chhunchha, Ahmedabad (IN)

(73) Assignee: Frimline Private Limited, Ahmedabad Gujarat (IN)

( * ) Notice: Subject to any disclaimer, the term of this patent is extended or adjusted under 35 U.S.C. 154(b) by 212 days.

(21) Appl. No.: 17/435,222

(22) PCT Filed: Jan. 25, 2021

(86) PCT No.: PCT/IB2021/050538
§ 371 (c)(1),
(2) Date: Aug. 31, 2021

(87) PCT Pub. No.: WO2021/152441
PCT Pub. Date: Aug. 5, 2021

(65) Prior Publication Data

US 2022/0370492 A1 Nov. 24, 2022

(30) Foreign Application Priority Data

Jan. 27, 2020 (IN) ............................. 202021003641

(51) Int. Cl.

| | |
|---|---|
| ***A61K 31/733*** | (2006.01) |
| ***A61K 31/202*** | (2006.01) |
| ***A61K 31/205*** | (2006.01) |
| ***A61K 31/718*** | (2006.01) |
| ***A61P 13/12*** | (2006.01) |

(52) U.S. Cl.
CPC .......... *A61K 31/733* (2013.01); *A61K 31/202* (2013.01); *A61K 31/205* (2013.01); *A61K 31/718* (2013.01); *A61P 13/12* (2018.01)

(58) Field of Classification Search
CPC ...... A61K 31/733; A61K 31/205; A61P 13/12
See application file for complete search history.

(56) References Cited

U.S. PATENT DOCUMENTS

| | | | |
|---|---|---|---|
| 2016/0051600 | A1 | 2/2016 | Martin Del Campo |
| 2019/0350226 | A1 | 11/2019 | Gebresalassie |

FOREIGN PATENT DOCUMENTS

| | | | |
|---|---|---|---|
| CN | 1504229 | A | 6/2004 |
| CN | 104740611 | A | 7/2015 |
| EP | 2754446 | A1 | 7/2014 |
| FR | 2851425 | A1 | 8/2004 |
| WO | 2002056710 | A1 | 7/2002 |
| WO | 2005056040 | A2 | 6/2005 |
| WO | 2019005422 | A1 | 1/2019 |

OTHER PUBLICATIONS

The John Hopkins, Patient guide to Diabetes (https://hopkinsdiabetesinfo.org/what-is-resistant-starch/; Jun. 7, 2018; Hereafter refereed as John Hopkins).*

Barbara U. Metzler-Zebeli et al.; "Effects of betaine, organic acids and inulin as single feed additives or in combination on bacterial populations in the gastrointestinal tract of weaned pigs"; Archives of Animal Nutrition; vol. 63; No. 6; Dec. 2009, pp. 427-441.

David O. McGregor et al., "Betaine supplementation decreases post-methionine hyperhomocysteinemia in chronic renal failure"; Kidney International; vol. 61; 2002; pp. 1040-1046.

* cited by examiner

*Primary Examiner* — Pancham Bakshi
(74) *Attorney, Agent, or Firm* — BakerHostetler

(57) ABSTRACT

The present invention relates to a composition/formulation for reducing uremic toxins, particularly protein bound uremic toxins in chronic kidney disease (CKD). More particularly, the pharmaceutical composition/formulation comprises a synergistic combination of Inulin and Betaine or their pharmaceutically acceptable salts for reducing protein bound uremic toxins. The present application also provides various compositions/formulations and process of preparing the same.

19 Claims, 2 Drawing Sheets

PHARMACEUTICAL COMPOSITION FOR REDUCING PROTEIN BOUND UREMIC TOXINS

CROSS-REFERENCE TO RELATED APPLICATIONS

This application is a National Stage Application of International Patent App. No. PCT/IB2021/050538, filed Jan. 25, 2021, which claims benefit to Indian Application No. 202021003641, filed Jan. 27, 2020, the entire disclosures of both of which are hereby incorporated by reference as if set forth in their entirety herein.

FIELD OF THE INVENTION

The present invention relates to compositions/formulations for reducing protein bound uremic toxins in chronic kidney disease (CKD). More particularly, the present invention relates to pharmaceutical composition/formulation comprising a synergistic combination of Inulin and Betaine or their pharmaceutically acceptable salts for reducing protein bound uremic toxins. The present application also provides various compositions/formulations and process of preparing the same.

BACKGROUND OF THE INVENTION

In the last two decades, renewed interest has emerged about the uremic syndrome. The uremic syndrome can be seen as inadequate removal and subsequent accumulation of organic products normally metabolized or excreted by the kidney in patients with chronic kidney disease (CKD).

The uremic syndrome is a result of the progressive decline in kidney function that leads to an accumulation of organic waste products. These waste products are usually called "uremic toxins" or "uremic retention solutes". Generally, protein-bound uremic toxins are produced from the metabolism of amino acids in the intestine.

In CKD, influx of urea and other retained toxins exerts a change in the gut microbiome. There is decreased number of beneficial bacteria that produce short-chain fatty acids, an essential nutrient for the colonic epithelium, concurrent with an increase in bacteria that produce uremic toxins such as indoxyl sulphate (IS), p-cresyl sulphate (PCS), and trimethylamine-N-oxide (TMAO).

Cardiovascular disease (CVD) is highly prevalent in patients with CKD. Cardiovascular mortality is responsible for approximately half of all death among CKD patients. Protein bound uremic toxins associated with CKD progression are independent cardiovascular risk factors in both non dialysis and dialysis patients.

There are currently five different gut derived uremic toxins that have been associated with CVD and mortality in CKD as well as other end-organ toxicity: indoxyl sulphate (IS), indole-3 acetic acid (IAA), p-cresyl sulphate (PCS), trimethylamine-N-oxide (TMAO), and phenylacetylglutamine (PAG).

PCS and IS are the major protein-bound uremic toxins, which have been reported not only to reduce endothelial proliferation but also to inhibit endothelial repair mechanisms. In addition, increasing evidence suggests these are a valuable predictor of cardiovascular events, infection event and all-cause mortality event in haemodialysis patients. However, there is also a significant association of serum PCS with CVD in CKD patients. PCS and IS seems a novel and important surrogate in CKD patients.

Existing Treatment & Disadvantages

Efforts have been made in understanding the mechanisms responsible for such uremic toxicity and to develop therapeutic interventions which can reduce the adverse effects of uremic toxins. An alternate means to lower their plasma levels is to reduce their production.

Dialysis processes have been devised for the separation of elements in a solution by diffusion across a semi-permeable membrane (diffusive solute transport) down a concentration gradient. Hemodialysis enables CKD patients with lost kidney function to survive for a longer period, and the advent of dialysis therapy has brought great gospel to many of the patients. Hemodialysis treatment utilizes the patient's blood to remove waste, toxins and excess water from the patient. However, unless renal transplantation is carried out, the dialysis therapy, which entails chronic complications such as itching and anemia, has to be continued for life and imposes a great mental and physical strain on the patients. It is often reported that accumulation of uremic substances in the body is involved in development of dialysis complications, and it is, therefore, a problem how to greatly and rapidly reduce harmful substances that are unable to be removed at all or sufficiently by dialysis from the body. Another drawback of hemodialysis is the need to utilize an anticoagulant during the treatment process, which may inevitably increase the risk of internal hemorrhages. More importantly, in CKD even via haemodialysis, the protein-bound uremic toxins cannot be excreted by the kidneys and are accumulated in the plasma. Moreover, dialysis is very expensive, inconvenient, time consuming and may occasionally produce one or more side effects. With a successful kidney transplant, a patient can live a more normal life with less long-term expense. However, there are also high costs associated with transplant surgery, the recovery period, and the continuous need for anti-rejection medications. Further, there are often a shortage of suitable donors.

Among the other possible efforts, nutrition management or dietary/food management has been recognized as one of the prominent ways for the management of CKD. Further, low-protein diet is often considered as a possible dietary approach to reduce the serum concentration of Uremic toxins. However, few studies suggest that the risk of malnutrition on low-protein diets in CKD population is even greater.

In addition to the above, attempts have also been made to remove uremic toxins in CKD patients by adsorption of such toxic substances in the gastrointestinal tract by Activated Charcoal. However, it also adsorbs enzymes, vitamins, mineral substances and the like. Furthermore, the Activated Charcoal treatment has a high pill burden and is associated with constipation and gastrointestinal upset.

In view of the aforementioned drawbacks and side-effects associated with the conventional treatments, it is desired to develop a formulation which not only will effectively reduce the protein bound ureinic toxins but also free from any side effects in CKD patients. Additionally, it is also desirable to have a composition/formulation which should be cost-effective and favourable to all age-group patients.

One potential means to suppress the production of such solutes (uremic toxins) is to increase dietary fiber intake. The term "fiber" comprises a variety of carbohydrates and related substances that are resistant to digestion in the small intestine. Colon microbes can break fiber down to short-chain fatty acids that provide energy to the host and for microbial growth. Increased fiber delivery to the colon may cause the microbes to utilize amino acids for growth, rather than to convert them to uremic solutes. In addition, fiber may alter the colon's microbial population in such a way as to decrease the production of undesirable solutes. Fiber may also reduce the colon transit time available for microbial metabolism.

Dietary fiber like Inulin may play a special role in renal disease since it could potentially reduce the colon microbial production of protein-derived uremic solutes without protein restriction. Presumably, fiber may affect production of nitrogenous solutes by providing energy to the colon microbes. Inulin is also a type of oligosaccharide called as Fructan. Fructans are a chain of fructose (sugar) molecules strung together. Inulin is fermented by bacteria that normalize the colon and is considered a prebiotic. Inulin and oligofructose have lower caloric values than typical carbohydrates because these are nondigestible by human intestinal enzymes. Thus, Inulin and oligofructose pass through the mouth, stomach and small intestine without being metabolized. Few studies indicate that almost all of the Inulin or oligofructose ingested enters the colon where it is totally fermented by the colonic microflora thereby resulting in increased utilization of the amino acids tyrosine and tryptophan which results in decreased production of p-Cresol and Indoles.

Betaines are fully N-methylated amino acids. Betaines are natural products that have an important function in both plant and animal metabolism. Betaine, also known as glycinebetaine or trimethylglycine, is a glycine derivative in which three methyl groups are bonded to the nitrogen atom of the glycine molecule. Betaine has a bipolar structure and it contains several chemically reactive methyl groups and thus, can donate it in enzyme-catalysed reactions. Betaine is involved in homocysteine metabolism. High homocysteine concentration in the blood is associated with an increased risk of cardiovascular disease. Plasma total homocysteine (tHcy) increases as renal function declines and more than 80% of people with end-stage renal disease are hyperhomocysteinemic. Betaine is used, among other things, as a feed additive and as a crop improver of plants under stress conditions, as well as in cosmetic, pharmaceutical and food industries.

RELATED PRIOR ARTS

CN1504229 discloses immunity toxin expelling powder for treating uremia wherein the powder comprises Astragalus root, Chinese angelica root, white atractylodes rhizome, root of red rooted saliva, corinth pink, and rheum officinale.

WO2005056040 relates to the in vivo treatment of uremic toxins in renal disease or dysfunction using uremic toxin-treating enzymes. The composition disclosed therein, may comprise one, two or more uremic toxin-treating enzymes such as urease, uricase or creatininase.

EP2754446 discloses a probiotic composition for reducing uremic toxins. The probiotic composition disclosed herein comprises of: at least one of *Lactobacillus plantarum* BCRC 12251, *Lactobacillus paracasei* BCRC 12188, *Streptococcus thermophilus* BCRC 13869 and *Enterococcus faecalis*. The said composition can be used for removal of blood uremic toxins such as protein-bound uremic toxins.

CN104740611 discloses a traditional Chinese medicine composition for treating uremia comprising of brain polypeptide hormone freeze-dried powder, humifuse euphorbia herb, fructus psoraleae and artemisia capillaries. The said composition is non-toxic, free of side effect and effective in improving uremia.

US20160051600 discloses use of a gelatinous mixture of probiotics and prebiotics with synergic symbiotic action for the treatment of chronic renal disease, for reducing the concentration of uremic toxins, improving the renal function of the patient with an increase in urea, creatinine, uric acid, p-cresols or indoles in the blood. The reference discloses the gelatinous mixture of probiotics and prebiotics containing water, cane sugar, glucose in liquid state, protein element, xanthan gum, prebiotic fiber of plant origin, vitamins, citrus seed extract, citric acid, malic acid, bifidobacterial, lactobacilli, colorant which is a mixture of fine powdered pigment with water and fragrance.

From the above disclosure and identified prior arts, it is clear that though options exist for reducing the level of uremic toxins including protein bound uremic toxins in CKD however, many such treatment options are associated with unpleasant or harmful side effects. Therefore, there is still a need for compositions/formulations that reduces protein bound uremic toxins in CKD patients without any side effects in humans or animals accompanied with good tolerability at an effective dose and good safety profile.

SUMMARY OF THE INVENTION

It has been found in the present invention that reducing protein bound uremic toxins in CKD patients (humans or animals) without any side effects accompanied with good tolerability at an effective dose and good safety profile is achieved through the administration of a stable composition/formulation comprising synergistic combination of Inulin with Betaine.

The present application accordingly provides compositions/formulations for reducing protein bound uremic toxins.

In a preferred aspect, the present application provides pharmaceutical compositions/formulations for reducing protein bound uremic toxins in chronic kidney disease (CKD).

The Inulin and Betaine combination of the present invention is able to provide a safe pharmaceutical composition/formulation with enhanced and/or synergistic effect compared to Inulin or Betaine or their pharmaceutically acceptable salts alone for reducing protein bound uremic toxins in CKD.

The present invention provides pharmaceutical compositions/formulations comprising a synergistic combination of Inulin or pharmaceutically acceptable salts thereof, and Betaine or pharmaceutically acceptable salts thereof.

One aspect of the present invention is to provide a composition/formulation for reducing the protein bound uremic toxins in CKD, wherein the said composition/formulation comprises a synergistic combination of Inulin and Betaine or their pharmaceutically acceptable salts.

Yet another aspect of the present invention is to provide a composition/formulation comprising a synergistic combination of Inulin and Betaine or their pharmaceutically acceptable salts for reducing the protein bound uremic toxins like p-cresyl sulfate (PCS) and indoxyl sulfate (IS) in CKD.

Another aspect of the present invention is to provide a pharmaceutical composition/formulation comprising a combination of Inulin and Betaine or their pharmaceutically acceptable salts in an optimized and/or judiciously selected synergistic ratio.

It is also an aspect of the present invention to provide suitable dosage form comprising a synergistic combination of Inulin and Betaine or their pharmaceutically acceptable salts for reducing protein bound uremic toxins in CKD.

Yet another aspect of the present invention is to provide suitable dosage regimen of composition/formulation comprising the synergistic combination of Inulin and Betaine or their pharmaceutically acceptable salts for reducing protein bound uremic toxins in CKD.

In a preferred aspect, the present invention provides pharmaceutical compositions/formulations comprising a synergistic combination of Inulin and Betaine or their pharmaceutically acceptable salts along with pharmaceutically acceptable excipients.

In one aspect, the composition/formulation of the present invention additionally comprises Resistant Starch, Omega-3 fatty acid, Short chain fatty acid(s) (SCFA) or a combination thereof.

In another aspect, the present invention provides a composition comprising Inulin or its pharmaceutically acceptable salts, Betaine or its pharmaceutically acceptable salts and additional active ingredients selected from Resistant Starch, Omega-3 fatty acid, Short chain fatty acid(s) (SCFA) or a combination thereof.

In a preferred aspect, the present invention provides pharmaceutical compositions/formulations comprising a synergistic combination of Inulin and Betaine or their pharmaceutically acceptable salts with additional active ingredients selected from Resistant Starch, Omega-3 fatty acid, Short chain fatty acid(s) (SCFA) along with pharmaceutically acceptable excipients.

In a further preferred aspect, the present invention provides any suitable dosage form for the composition/formulation of the present invention. Preferably, the composition/formulation of this invention is formulated as an oral dosage form.

DETAILED DESCRIPTION OF THE INVENTION

Figure 1:
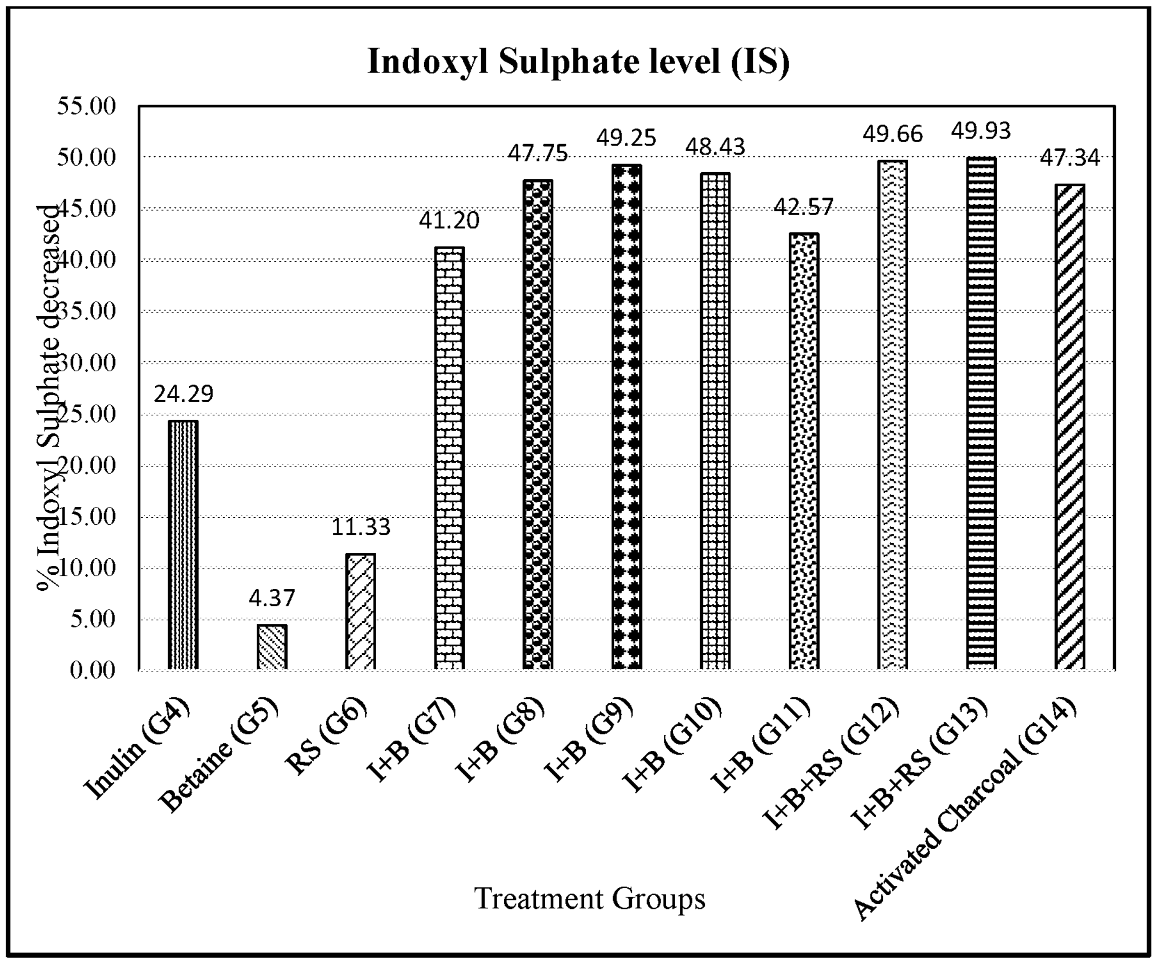
FIG. 1: Effect of test composition/formulation on the level of Indoxyl Sulphate (IS) compared to disease control in 5/6 Nephrectomy induced chronic kidney disease in rats.
Figure 2:
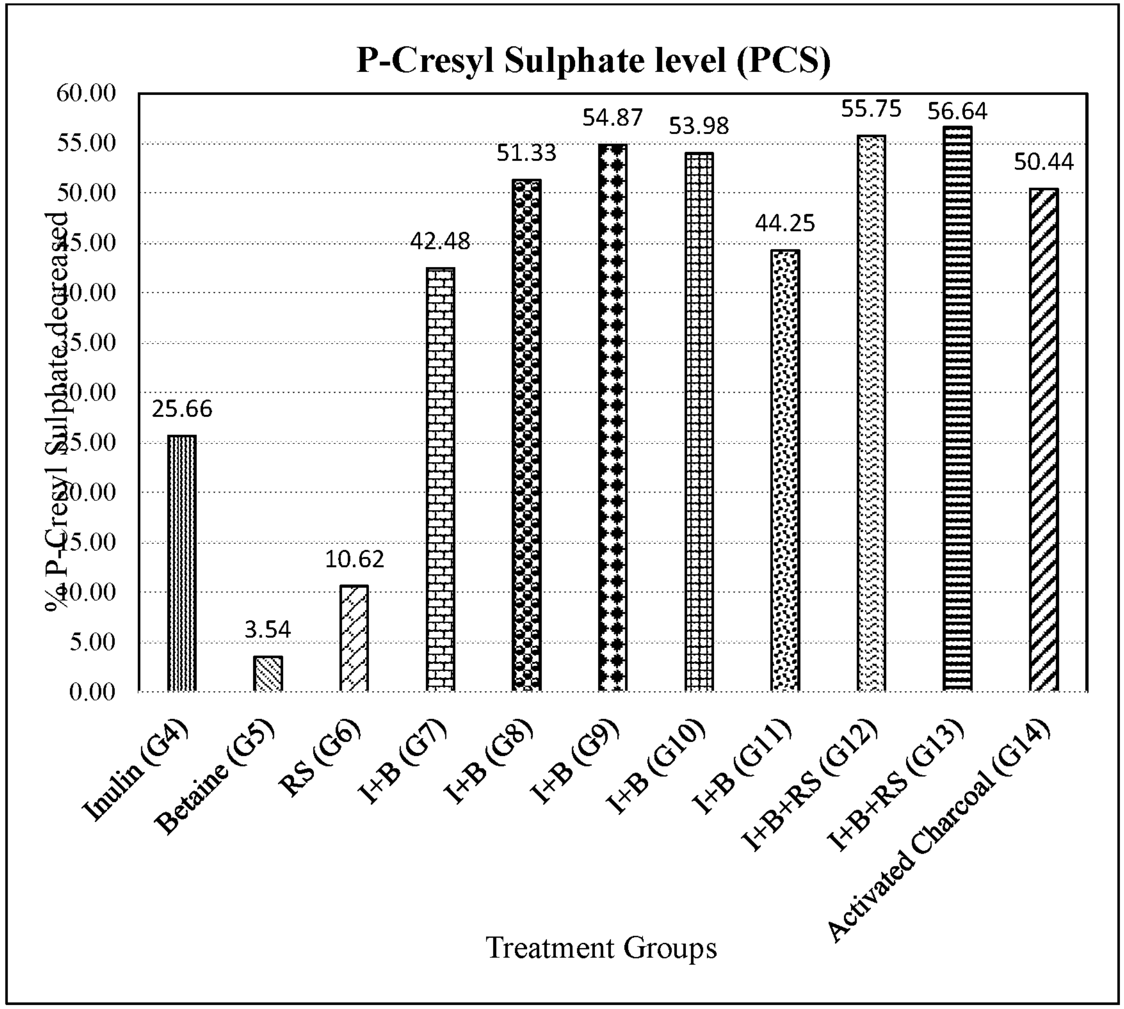
FIG. 2: Effect of test composition/formulation on the level of P-Cresyl Sulphate (PCS) compared to disease control in 5/6 Nephrectomy induced chronic kidney disease in rats.

While the invention is susceptible to various modifications and alternative forms, specific embodiments thereof are described in detail in example's section below. It should be understood, however that it is not intended to limit the invention to the particular forms disclosed, but on the contrary, the invention is to cover all modifications, equivalents, and alternatives falling within the scope of the invention.

It is further to be understood that all terminology used herein is for the purpose of describing particular embodiments only and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a," "an" and "the" include plural reference unless the context clearly dictates otherwise.

Unless otherwise specified, all percentages and amounts expressed herein and elsewhere in the specification should be understood to refer to percentages by weight. The amounts given are based on the active weight of the material.

The term 'composition' includes pharmaceutical compositions, nutraceutical compositions, dietary supplement compositions, medicinal compositions, nutritional supplement compositions, food for special medical purpose and any other suitable composition.

The term 'formulation' includes pharmaceutical formulations, nutraceutical formulations, dietary supplement formulations, medicinal formulations, nutritional supplement formulations, food for special medical purpose and any other suitable formulation. The terms composition and formulation are used interchangeably unless the context requires otherwise.

The term "pharmaceutically acceptable salts" as used herein represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically acceptable salts" refers to the relatively non-toxic, inorganic and organic acid addition salts of compounds as well as solvates, co-crystals, polymorphs, derivatives and the like of the salts.

The present invention is directed to a pharmaceutical composition/formulation comprising a synergistic combination of Inulin or pharmaceutically acceptable salts thereof and Betaine or pharmaceutically acceptable salts thereof for reducing protein bound uremic toxins, like p-cresyl sulfate (PCS) and indoxyl sulfate (IS), in chronic kidney disease (CKD). In this regard, the inventors carried out an extensive research along with pre-clinical studies and found that the combination of Inulin and Betaine or their pharmaceutically acceptable salts provides synergistic effect on reduction of protein bound uremic toxins, like PCS and IS, in CKD.

Some studies of the prior art show the effect of Inulin in lowering plasma concentrations of IS and PCS in CKD. However, the role of Betaine in reducing protein bound uremic toxins, like IS and PCS, in CKD is not yet known. Further the effects of composition/formulation of the present invention comprising a synergistic combination of Inulin and Betaine or their pharmaceutically acceptable salts, which drastically/significantly improves the reduction of protein bound uremic toxins, have not been reported.

The synergistic combination of the present invention is able to provide a safe pharmaceutical composition/formulation comprising of Inulin with Betaine or their pharmaceutically acceptable salts with enhanced and/or synergistic effects for reducing protein bound uremic toxins in CKD compared to Inulin or Betaine or their pharmaceutically acceptable salts alone.

Within the scope of the present invention, it has now been found that the synergistic combination/formulation of Inulin with Betaine or their pharmaceutically acceptable salts have surprising and particularly advantageous effects. This makes them particularly suitable for reducing protein bound uremic toxins in CKD.

Inulin can be taken in its any suitable form. More particularly, Inulin can be selected from its pharmaceutically acceptable salts, esters, polymorphs or derivatives. In particular features, the present invention employs Inulin Propionate Ester (IPE), Oligofructose enriched Inulin, Inulin sulphate or Inulin.

In an embodiment, the pharmaceutical composition/formulation of the present invention comprises Inulin or pharmaceutically acceptable salts thereof, wherein the amount of Inulin or pharmaceutically acceptable salts thereof in the composition/formulation of the present invention is at least 90% by wt. of the composition. In further embodiment, the amount of Inulin or pharmaceutically acceptable salts thereof in the pharmaceutical composition/formulation of the present invention is less than or equal to 99% by wt. of the composition. In yet another embodiment, the amount of Inulin or pharmaceutically acceptable salts thereof that can be used in the pharmaceutical composition/formulation of the present invention ranges from 90 to 99% by wt. of the composition/formulation. In another embodiment, the amount of Inulin or pharmaceutically acceptable salts thereof ranges from 90 to 95% by wt. of the composition. In further embodiment, the amount of Inulin or pharmaceutically acceptable salts thereof ranges from 95 to 99% by wt. of the composition.

In another embodiment, the pharmaceutical composition/formulation of the present invention comprises Inulin or pharmaceutically acceptable salts thereof, wherein the amount of Inulin or pharmaceutically acceptable salts thereof in the composition/formulation of the present invention is at least 1 gm per unit dose. In another embodiment, the composition/formulation of the present invention comprises of less than or equal to 20 gm of Inulin or pharmaceutically acceptable salts thereof per unit dose. In yet another embodiment, the amount of Inulin or pharmaceutically acceptable salts thereof that can be used in the pharmaceutical composition/formulation of the present invention ranges from 1 gm to 20 gm per unit dose. In a preferred embodiment, the amount of Inulin or pharmaceutically acceptable salts thereof ranges from 5 gm to 20 gm per unit dose. In a preferred embodiment, the intake of Inulin or pharmaceutically acceptable salts thereof is about 1 gm to 20 gm per day.

The composition of the present invention also includes Betaine in synergistic combination with Inulin, wherein Betaine may be involved in homocysteine metabolism. Betaine can be taken in its any suitable form. Particularly, Betaine can be selected from its pharmaceutically acceptable salts, esters, polymorphs or derivatives. More particularly, Betaine can be in the hygroscopic form or non-hygroscopic form. Specifically, Betaine can be in the form of monohydrate, anhydrous form, Glycine betaine or pharmaceutically acceptable salts thereof, like Betaine Hydrochloride.

In an embodiment, the pharmaceutical composition/formulation of the present invention comprises Betaine or pharmaceutically acceptable salts thereof, wherein the amount of Betaine in the composition/formulation of the present invention is at least 0.5% by wt. of the composition. In another embodiment, the amount of Betaine or pharmaceutically acceptable salts thereof in the composition/formulation of the present invention is less than or equal to 10% by wt. of the composition. In yet another embodiment, the composition/formulation of the present invention comprises of Betaine or pharmaceutically acceptable salts thereof in judiciously selected amount ranging from 0.5 to 10% by wt. of the composition. In another embodiment, the amount of Betaine or pharmaceutically acceptable salts thereof ranges from 0.5 to 5% by wt. of the composition. In further embodiment, the amount of Betaine or pharmaceutically acceptable salts thereof ranges from 5 to 10% by wt. of the composition.

In another embodiment, the pharmaceutical composition/formulation of the present invention comprises Betaine or pharmaceutically acceptable salts thereof, wherein the amount of Betaine or pharmaceutically acceptable salts thereof in the composition/formulation of the present invention is at least 1 mg per unit dose. In another embodiment, the composition/formulation of the present invention comprises of less than or equal to 1000 mg of Betaine or pharmaceutically acceptable salts thereof per unit dose. In yet another embodiment, the amount of Betaine or pharmaceutically acceptable salts thereof that can be used in the pharmaceutical composition/formulation of the present invention ranges from 1 to 1000 mg per unit dose. In a preferred embodiment, the amount of Betaine or pharmaceutically acceptable salts thereof ranges from 1 mg to 1000 mg per unit dose. In a preferred embodiment, the intake of Betaine or pharmaceutically acceptable salts thereof is about 1 mg to 1000 mg per day.

In yet another embodiment, the pharmaceutical composition/formulation of the present invention comprises a synergistic combination of Inulin or pharmaceutically acceptable salts thereof ranging from 90 to 99% by wt. of the composition and Betaine or pharmaceutically acceptable salts thereof ranging from 0.5 to 10% by wt. of the composition.

The composition/formulation of the present invention uses Betaine or pharmaceutically acceptable salts thereof in combination with Inulin or pharmaceutically acceptable salts thereof to provide synergistic effect and enhances the effect of Inulin or pharmaceutically acceptable salts thereof in reducing protein bound uremic toxins in CKD. In another embodiment, the composition/formulation of the present invention uses Inulin or pharmaceutically acceptable salts thereof in combination with Betaine or pharmaceutically acceptable salts thereof in a judiciously optimized ratio (w/w) of 1:0.006 to 1:0.111 to synergistically reduce the levels of protein bound uremic toxins in CKD.

In preferred embodiment, the pharmaceutical composition/formulation of the present invention comprises a synergistic combination of Inulin and Betaine or their pharmaceutically acceptable salts with pharmaceutically acceptable excipients.

In yet another embodiment, the composition/formulation of the present invention additionally comprises other active ingredients such as Resistant Starch, Omega-3 fatty acid, Short chain fatty acid(s) (SCFA), or any combination thereof.

In yet another embodiment, the composition/formulation of the present invention comprises a synergistic combination of Inulin and Betaine or their pharmaceutically acceptable salts with additional active ingredients and pharmaceutically acceptable excipients. The additional active ingredients such as Resistant Starch, Omega-3 fatty acid, short chain fatty acid(s) (SCFA) or any combination thereof may further enhance the effect of synergistic combination of Inulin and Betaine or their pharmaceutically acceptable salts.

In preferred embodiment, the pharmaceutical composition/formulation of the present invention comprises a synergistic combination of Inulin and Betaine or their pharmaceutically acceptable salts with Resistant Starch. In another preferred embodiment, the pharmaceutical composition/formulation of the present invention comprises a synergistic combination of Inulin and Betaine or their pharmaceutically acceptable salts with Resistant Starch and pharmaceutically acceptable excipients.

In an embodiment, the amount of Resistant Starch that can be used in the pharmaceutical composition/formulation of the present invention ranges from 0.8 to 9% by wt. of the composition/formulation.

In another embodiment, the amount of Resistant Starch that can be used in the pharmaceutical composition/formulation of the present invention ranges from 0.5 gm to 20 gm per unit dose. In a preferred embodiment, the amount of Resistant Starch intake is 0.5 gm to 20 gm per day.

In a preferred embodiment, the pharmaceutical composition/formulation of the present invention comprises a synergistic combination of Inulin and Betaine or their pharmaceutically acceptable salts with Omega-3 fatty acid. In another preferred embodiment, the pharmaceutical composition/formulation of the present invention comprises a synergistic combination of Inulin and Betaine or their pharmaceutically acceptable salts with Omega-3 fatty acid and pharmaceutically acceptable excipients.

In one embodiment, the Omega-3 fatty acid can be Alpha-linolenic acid (ALA), Eicosapentaenoic acid (EPA), Docosahexaenoic acid (DHA) or a combination thereof. In a preferred embodiment, the amount of Omega-3 fatty acid that can be used in the pharmaceutical composition/formulation of the present invention ranges from 0.89 to 9% by wt. of the composition/formulation.

In a preferred embodiment, the amount of Omega-3 fatty acid that can be used in the pharmaceutical composition/formulation of the present invention ranges from 100 mg to 3 gm per unit dose. In a preferred embodiment, the amount of Omega-3 fatty acid intake is 100 mg to 3 gm per day.

In preferred embodiment, the pharmaceutical composition/formulation of the present invention comprises a synergistic combination of Inulin and Betaine or their pharmaceutically acceptable salts with SCFA or pharmaceutically acceptable salts thereof. In another preferred embodiment, the pharmaceutical composition/formulation of the present invention comprises a synergistic combination of Inulin and Betaine or their pharmaceutically acceptable salts with SCFA and pharmaceutically acceptable excipients.

In one embodiment, SCFA are linear or branched C1-C5 monocarboxylic organic acids such as acetic, propionic, butyric and isovaleric acids. The pharmaceutically acceptable salts of the SCFA includes but are not limited to sodium propionate, sodium butyrate, etc. In another embodiment, SCFA can be used in the pharmaceutical composition/formulation of the present invention ranging from 0.8 to 8.2% by wt. of the composition/formulation.

In the preferred embodiment, the amount of SCFA that can be used in the pharmaceutical composition/formulation of the present invention ranges from 150 mg to 3 gm per unit dose. In a preferred embodiment, the amount of SCFA intake is about 150 mg to 3 gm per day.

In yet another embodiment, the pharmaceutical compositions/formulations of the present invention are prepared/provided in any suitable administrable form such as solid and liquid dosage form. The solid dosage form includes oral dosage form such as powder, tablet, capsule, hard capsule filled with liquid or solid, soft capsule, pill, sachet, granule etc. The liquid dosage form includes oral dosage form such as solution, suspension, emulsion, syrup, etc.

The term "excipient" or "suitable excipient" used herein means a pharmacologically inactive component. The excipients that are useful in preparing pharmaceutical composition/formulation of the present invention are generally safe and non-toxic. Reference to an excipient includes both one and more than one such excipient. Co-processed excipients are also covered under the scope of present invention. In yet another embodiment, the composition/formulation of the present invention contains pharmaceutically acceptable carriers/vehicles/diluents or excipients to make desired composition/formulation or dosage form. The "pharmaceutically acceptable carriers/vehicles/diluents or excipients" as used herein is intended to mean, without limitation, any adjuvants, carriers, sweetening agents, flavouring agents (flavour enhancers), diluents, preservative, dye/colorants, surfactants, wetting agents, dispersing agents, suspending agents, complexing agents, stabilizers, isotonic agent, solvent, emulsifier, encapsulating agent, polymers, coating agent, wax, encapsulating polymeric delivery systems. Excipients may also include antiadherents, antioxidants, binders, pH-modifier, solvents, coatings, compression aids, disintegrants, emollients, fillers, film formers, fragrances, glidants (flow enhancers), lubricants, preservatives, sorbents, anticaking agent, food additives, or waters of hydration.

In a preferred embodiment, the pharmaceutically acceptable excipients are flavouring agents and sweetening agents.

The sweetening agents herein include but are not limited to lactitol, maltitol, mannitol, sorbitol, sucrose, xylitol, acesulfame potassium, alitame, aspartame, compressible sugar, confectioner's sugar, dextrose, erythritol, fructose, glycerin, glycine, isomalt, liquid glucose, maltose, neohesperidin dihydrochalcone, neotame, saccharin, saccharin sodium, sodium cyclamate, sucralose, tagatose, thaumatin, trehalose or the like. The amount of sweetener in the pharmaceutical composition/formulation of the present invention is used in a range of about 0.01 to 1% by wt. of the composition/formulation.

The flavouring agent as used may be orally acceptable natural or synthetic flavors, natural essences, extractable essences, essential oils or a mixture thereof not limited to adipic acid, n-butyl lactate, confectioner's sugar, denatonium benzoate, dibutyl sebacate, ethyl acetate, ethyl lactate, ethyl maltol, ethyl vanillin, ethyl cellulose, fumaric acid, leucine, malic acid, maltol, menthol, methionine, monosodium glutamate, phosphoric acid, propionic acid, sodium acetate, sodium lactate, sodium propionate, tartaric acid, thymol, triethyl citrate, vanillin, Vanilla, Pineapple, Mixed fruit, Banana, Orange, geraniol, geranium essence, eucalyptol essential oil, almond oil, fruit flavours, honey or the like. The amount of flavouring agent in the pharmaceutical composition/formulation of the present invention is used in a range of 0.01 to 3% by wt. of the composition/formulation.

The diluent is selected from microcrystalline cellulose, lactose (anhydrous/monohydrate/spray dried), cellulose powder, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, compressible sugar, confectioner's sugar, corn starch, pregelatinized starch, dextrates, dextrin, dextrose, erythritol, ethylcellulose, fructose, fumaric acid, glyceryl palmitostearate, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, sterilizable maize, sucrose, sugar spheres, sulfobutylether $\beta$-cyclodextrin, talc, tragacanth, trehalose, xylitol or the like. The amount of diluent in the pharmaceutical composition/formulation of the present invention ranges from 0 to 10% by wt. of the composition/formulation.

The binder is selected from Hypromellose, acacia, agar, alginic acid, calcium carbonate, calcium lactate, carbomers, carboxymethylcellulose sodium, carrageenan, cellulose acetate phthalate, ceratonia, chitosan, copovidone, corn starch, pregelatinized starch, cottonseed oil, dextrates, dextrin, dextrose, ethylcellulose, gelatin, glyceryl behenate, guar gum, hydrogenated vegetable oil type I, hydroxyethyl cellulose, hydroxy-ethylmethyl cellulose, hydroxypropyl cellulose, lactose, liquid glucose, low-substituted Hypromellose, magnesium aluminum silicate, maltodextrin, maltose, methyl-cellulose, microcrystalline cellulose, pectin, poloxamer, polycarbophil, polydextrose, polyethylene oxide, polymethacrylates, povidone, sodium alginate, stearic acid, sucrose, sunflower oil, tricaprylin, vitamin E polyethylene glycol succinate, zein or the like. The amount of binder in the pharmaceutical composition/formulation of the present invention ranges from 0 to 10% by wt. of the composition/formulation.

The disintegrating agent is selected from croscarmellose sodium, crospovidone, carboxymethyl cellulose (sodium/calcium), sodium starch glycolate, alginic acid, calcium alginate, cellulose powdered, chitosan, colloidal silicon dioxide, corn starch, docusate sodium, glycine, guar gum, hydroxypropyl cellulose low-substituted, magnesium aluminum silicate, methylcellulose, microcrystalline cellulose, polacrilin potassium, povidone, sodium alginate, pregelatinized starch or the like. The amount of disintegrating agent in the pharmaceutical composition/formulation of the present invention ranges from 0 to 10% by wt. of the composition/formulation.

The lubricant is selected from magnesium stearate, zinc stearate, calcium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition/formulation of the present invention ranges from 0 to 5% by wt. of the composition/formulation.

The glidant is selected from colloidal silicon dioxide, talc, calcium phosphate tribasic, cellulose powdered, magnesium oxide, magnesium silicate, magnesium trisilicate or the like. The amount of Glidant in the pharmaceutical composition/formulation of the present invention ranges from 0 to 5% by wt. of the composition/formulation.

The coating layer for the composition/formulation of the present invention is selected from film coating, seal coating or enteric coating. The total amount of coating agent in the pharmaceutical composition/formulation of the present invention ranges from 0 to 10% by wt. of the composition/formulation.

The seal coating agent is selected from Instamoistshield (Hydroxypropyl methyl cellulose, Polyethylene glycol, Talc, Titanium dioxide, Ethyl cellulose), gelatin, copovidone, hydroxyethyl cellulose, ethyl cellulose, vanillin, hydroxypropyl cellulose, guar gum, maleic acid, Hypromellose, polymethacrylates, Methyl cellulose or the like. The amount of seal coating agent in the pharmaceutical composition/formulation of the present invention ranges from 0 to 3.0% by wt. of the composition/formulation.

The enteric coating agent is selected from Instacoat EN HPMC P (Hydroxypropyl methyl cellulose Phthalate, Polyethylene glycol, Titanium dioxide, Red Iron oxide), Methacrylate copolymer, shellac, sodium alginate, acetyltributyl citrate, carbomers, cellulose acetate phthalate, guar gum, hypromellose acetate succinate, hypromellose phthalate, polymethacrylates, polyvinyl acetate phthalate, potassium chloride, glycerin, Sureteric, tributyl citrate, triethyl citrate, triolein, white wax, zein, cellulose acetate phthalate with ethyl cellulose, chitosan, hydroxypropyl cellulose or the like. The amount of enteric coating agent in the pharmaceutical composition/formulation of the present invention ranges from 0 to 10.0% by wt. of the composition/formulation.

The film coating agent is selected from Instacoat Universal (Hydroxypropyl methyl cellulose, Polyethylene glycol, Talc, Titanium dioxide), guar gum, Hypromellose, Povidone, hydroxypropyl cellulose, cellulose acetate, polydextrose, Ethyl cellulose, methylcellulose, gelatin, glycerin, maltodextrin or the like. The amount of film coating agent in the pharmaceutical composition/formulation of the present invention ranges from 0 to 3.0% by wt. of the composition/formulation.

The solvent is selected from water, alcohol, isopropyl alcohol, propylene glycol, almond oil, benzyl alcohol, benzyl benzoate, butylene glycol, carbon dioxide, castor oil, corn oil (maize), cottonseed oil, dibutyl phthalate, diethyl phthalate, dimethyl ether, albumin, dimethyl phthalate, dimethyl sulfoxide, dimethylacetamide, ethyl acetate, ethyl lactate, ethyl oleate, glycerin, glycofurol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl 35 castor oil, propylene carbonate, pyrrolidone, safflower oil, sesame oil, soybean oil, sunflower oil, triacetin, tricaprylin, triethanolamine, triethyl citrate, triolein, water-miscible solvents or the like. The amount of solvent in the pharmaceutical composition/formulation of the present invention is used in a quantity sufficient.

The solubilizing agent is selected from polysorbate 80, sodium lauryl sulfate, anionic emulsifying wax, glycerol, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E polyethylene glycol succinate, microcrystalline cellulose, carboxymethylcellulose sodium, diethanolamine, ethylene glycol palmitostearate, glycerin monostearate, hypromellose, hypromellose acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, meglumine, poloxamer, pyrrolidone, sodium bicarbonate, stearic acid, sulfobutylether β-cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like. The amount of Solubilizing Agent in the pharmaceutical composition of the present invention ranges from 0 to 5% by wt. of the composition.

The anti-oxidant is selected from propyl gallate, lecithin, vitamin E, tocopherol, sesamin, sesamol, sesamolin, alpha tocopherol, ascorbic acid, ascorbyl palmitate, fumaric acid, malic acid, sodium metabisulphite, butylated hydroxyanisole (BHA), butylated hydroxytoluene (BHT) or the like.

The amount of anti-oxidant in the pharmaceutical composition of the present invention ranges from 0 to 1% by wt. of the composition.

The preservative is selected from diazolidinyl urea, iodopropnyl butylcarbamate, vitamin E (alpha-tocopherol) and its derivatives including vitamin E acetate (alpha-tocopherol acetate), vitamin C (ascorbic acid), butylated hydroxytoluene (BHT), butylated hydroxyanisole (BHA), esters of p-hydroxy benzoic acid, ethylparaben, propylparaben, butylparaben or the like. The amount of preservative in the pharmaceutical composition of the present invention ranges from 0 to 1% by wt. of the composition.

In another feature, the excipients are present in quantity sufficient to make suitable composition/formulation or dosage form.

The active components that are present in the composition/formulation can be used in the most appropriate physical state for the production of a suitable form for administration. The composition of the present invention is preferably intended for oral administration and the preferred form is the solid or liquid form. In order to produce these solid forms, in particular powder or granules in sachet form or for filling in capsule or tablets, the ingredients which are naturally in liquid state, may be suitably adapted for preparation of solid forms. For e.g., since butyric acid is a liquid, a solid salt of the acid such as, for example, calcium butyrate, sodium butyrate, Sodium Propionate or Beta hydroxybutyrate may be used or the acid itself may be supported on a solid substrate of inert material by the known spray-dry technique or by adsorption. As solid substrates, it is possible to use the excipients that are normally used for the preparation of powders or granules such as, for example, pectin, monosaccharide and polysaccharide sugars, alginates, microcrystalline cellulose, gum arabic, maize starch, pre-gelatinized starch, alkyl derivatives or hydroxyalkyl derivatives of cellulose with low, medium and high viscosity, monoprotic and polyprotic mineral salts, cyclodextrin, alkylcyclodextrin, hydroxyalkylcyclodextrin, pyrrolidones or derivatives, monocarboxylic organic salts and/or esters, polycarboxylic organic salts and/or esters, inorganic substrates such as colloidal silica, talc and organic and inorganic ion-exchange resins. In order to produce a powder from a liquid, atomization is performed by the drying of a suspension of liquid butyric acid and solid substrate by the spray-dry technique, or butyric acid is adsorbed on one of the above-mentioned substrates.

Some of the exemplary compositions of the present invention are described below:

Composition/Formulation 1—Synergistic Combination/Blend

| Sr. No. | Ingredients | Amount (% w/w) |
|---|---|---|
| 1. | Inulin or pharmaceutically acceptable salts thereof | 90 to 99 |
| 2. | Betaine or pharmaceutically acceptable salts thereof | 0.5 to 10 |

Composition/Formulation 2—Synergistic Combination/Blend

| Sr. No. | Ingredients | Amount (% w/w) |
|---|---|---|
| 1. | Inulin or pharmaceutically acceptable salts thereof | 90 to 99 |
| 2. | Betaine or pharmaceutically acceptable salts thereof | 0.5 to 10 |
| 3. | Resistant starch | 0.8 to 9 |

Composition/Formulation 3—Synergistic Combination/Blend

| Sr. No. | Ingredients | Amount (% w/w) |
|---|---|---|
| 1. | Inulin or pharmaceutically acceptable salts thereof | 90 to 99 |
| 2. | Betaine or pharmaceutically acceptable salts thereof | 0.5 to 10 |
| 3. | Omega-3 fatty acid | 0.89 to 9 |

Composition/Formulation 4—Synergistic Combination/Blend

| Sr. No. | Ingredients | Amount (% w/w) |
|---|---|---|
| 1. | Inulin or pharmaceutically acceptable salts thereof | 90 to 99 |
| 2. | Betaine or pharmaceutically acceptable salts thereof | 0.5 to 10 |
| 3. | Short chain fatty acid (SCFA) or pharmaceutically acceptable salts thereof | 0.8 to 8.2 |

Composition/Formulation 5—Synergistic Combination/Blend

| Sr. No. | Ingredients | Amount (% w/w) |
|---|---|---|
| 1. | Inulin or pharmaceutically acceptable salts thereof | 90 to 99 |
| 2. | Betaine or pharmaceutically acceptable salts thereof | 0.5 to 10 |
| 3. | Resistant Starch | 0.8 to 9 |
| 4. | Omega-3 fatty acid | 0.89 to 9 |
| 5. | Short chain fatty acid (SCFA) or pharmaceutically acceptable salts thereof | 0.8 to 8.2 |

General Process for Preparation of the Formulations of the Present Invention

The present invention also provides a process for preparing the pharmaceutical composition/formulation of the present invention. Once the composition of the present invention has been prepared in the present application, a person skilled in the art can further adapt the below provided process, with suitable modifications, for the preparation of the pharmaceutical compositions/formulations of the present invention.

General Process of Preparation

Manufacturing Procedure:—(Powder Dosage Form)

1. Weigh accurately all the ingredients in separate containers.
2. Sift previously weighed ingredients separately through sieve #40.
3. Mix all sifted materials using Blender for about 30 min at about 20 RPM and store the blend in double polyethylene lined container and seal the polyethylene bags properly and keep silica bag between polybags to protect from moisture.
4. Fill the blend obtained in step 3 in sachet or other suitable packaging material.
5. Temperature of NMT 25° C. and humidity condition of 40% RH is maintained at all stages of manufacturing.

Manufacturing Procedure:—(Capsule Dosage Form)

1. Weigh accurately all the Ingredients in separate containers.
2. Pass previously weighed ingredients separately through sieve #30.
3. Mix content of step 2 in Blender with slow speed.
4. Pass previously weighed lubricant through sieve #40. Transfer it to blender & run blender.
5. Fill and Seal the blend obtained in step 4 with HPMC capsule shells.
6. Transfer the filled capsules into the hopper of polishing and visual inspection machine to remove the debris of powder sticking with the capsule shells.
7. Temperature of NMT 25° C. and humidity condition of 40% RH is maintained at all stages of manufacturing.

Manufacturing Procedure:—(Tablet Dosage Form)

1. Individually weigh the ingredients and sieve through a suitable sieve.
2. Mix the previously weighed ingredients.
3. Prepare a dough by adding a binder solution to the mixed ingredients and sieve the dough to obtain granules.
4. Dry the granules obtained in step 3 till the level of dryness (LOD) is reduced to 1.3 to 1.7% w/w to obtain semi dried granules.
5. Sieve the semi dried granules obtained in step 4 through a suitable sieve.
6. Add lubricants or glidants to the semi dried granules obtained in step 5 and compress the granules into tablet.
7. The process further comprises preparing the seal coating and enteric coating solution for enteric coated tablets and film coating solution for film coated tablets.
8. Temperature of NMT 25° C. and humidity condition of 40% RH is maintained at all stages of manufacturing.

Manufacturing Procedure:—(Solution Dosage Form)

1. Weigh accurately all the ingredients in separate containers.
2. Sift previously weighed ingredients separately through sieve #40.
3. Add all the sifted ingredients to the mixer along with the solvent.
4. Mix well and continue the stirring till a clear solution is obtained.
5. Temperature of NMT 25° C. and humidity condition of 40% RH is maintained at all stages of manufacturing.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention. The following examples are set forth to illustrate the pharmaceutical compositions/formulations of the present invention. The examples also provide and/or demonstrate efficacy or synergistic effect of the pharmaceutical composition/formulation of the present invention. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Example 1

| Sr. No. | Ingredients | % w/w |
|---|---|---|
| 1 | Inulin | 88.52 |
| 2 | Betaine | 11.46 |
| 3 | Flavouring agent (Orange) | 0.01 |
| 4 | Sweetening agent (Xylitol) | 0.01 |
| | Final Wt. of Powder | 100 |

Example 2

| Sr. No. | Ingredients | % w/w |
|---|---|---|
| 1 | Inulin | 90.00 |
| 2 | Betaine | 10.00 |
| | Final Wt. of Powder | 100 |

Example 3

| Sr. No. | Ingredients | % w/w |
|---|---|---|
| 1 | Inulin | 95.97 |
| 2 | Betaine | 2.88 |
| 3 | Flavouring agent (Vanilla) | 0.96 |
| 4 | Sweetening agent (Sucralose) | 0.19 |
| | Final Wt. of Powder | 100 |

Example 4

| Sr. No. | Ingredients | % w/w |
|---|---|---|
| 1 | Inulin | 98.99 |
| 2 | Betaine | 0.99 |

-continued

| Sr. No. | Ingredients | % w/w |
|---|---|---|
| 3 | Flavouring agent (Mixed fruit) | 0.01 |
| 4 | Sweetening agent (Sucrose) | 0.01 |
| | Final Wt. of Powder | 100 |

Example 5

| Sr. No. | Ingredients | % w/w |
|---|---|---|
| 1 | Inulin | 99.67 |
| 2 | Betaine | 0.11 |
| 3 | Flavouring agent (Banana) | 0.11 |
| 4 | Sweetening agent (Aspartame) | 0.11 |
| | Final Wt. of Powder | 100 |

Example 6

| Sr. No. | Ingredients | % w/w |
|---|---|---|
| 1 | Inulin | 90.01 |
| 2 | Betaine | 0.90 |
| 3 | Resistant Starch | 9.00 |
| 4 | Flavouring agent (Mixed fruit) | 0.09 |
| | Final Wt. of Powder | 100 |

Example 7

| Sr. No. | Ingredients | % w/w |
|---|---|---|
| 1 | Inulin Propionate Ester | 94.07 |
| 2 | Betaine Hydrochloride | 0.94 |
| 3 | Resistant Starch | 4.70 |
| 4 | Flavouring agent (Vanilla) | 0.09 |
| 5 | Sweetening agent (Aspartame) | 0.19 |
| | Final Wt. of Powder | 100 |

Example 8

| Sr. No. | Ingredients | % w/w |
|---|---|---|
| 1 | Inulin | 90.01 |
| 2 | Betaine | 0.90 |
| 3 | Omega-3 fatty acid | 9.00 |
| 4 | Flavouring agent (Orange) | 0.09 |
| | Final Wt. of Powder | 100 |

Example 9

| Sr. No. | Ingredients | % w/w |
|---|---|---|
| 1 | Inulin Propionate Ester | 97.86 |
| 2 | Betaine Anhydrous | 0.93 |
| 3 | Omega-3 fatty acid | 0.93 |
| 4 | Flavouring agent (Mixed fruit) | 0.09 |
| 5 | Sweetening agent (Mannitol) | 0.19 |
| | Final Wt. of Powder | 100 |

Example 10

| Sr. No. | Ingredients | % w/w |
|---|---|---|
| 1 | Inulin | 90.66 |
| 2 | Betaine | 0.91 |
| 3 | SCFA (Sodium Butyrate) | 8.16 |
| 4 | Flavouring agent (Banana) | 0.09 |
| 5 | Sweetening agent (Sorbitol) | 0.18 |
| | Final Wt. of Powder | 100 |

Example 11

| Sr. No. | Ingredients | % w/w |
|---|---|---|
| 1 | Inulin | 98.89 |
| 2 | Betaine | 0.56 |
| 3 | Flavouring agent (Mixed fruit) | 0.22 |
| 4 | Sweetening agent (Sucrose) | 0.33 |
| | Final Wt. of Powder | 100 |

Example 12

| Sr. No. | Ingredients | % w/w |
|---|---|---|
| 1 | Oligofructose enriched Inulin | 95.45 |
| 2 | Betaine Hydrochloride | 4.09 |
| 3 | Flavouring agent (Orange) | 0.18 |
| 4 | Sweetening agent (Sucralose) | 0.27 |
| | Final Wt. of Powder | 100 |

Example 13

| Sr. No. | Ingredients | % w/w |
|---|---|---|
| 1 | Inulin | 95.15 |
| 2 | Betaine | 1.90 |
| 3 | Omega-3 fatty acid | 1.90 |
| 4 | Resistant Starch | 0.95 |
| 5 | Flavouring agent (Banana) | 0.10 |
| | Final Wt. of Powder | 100 |

Example 14

| Sr. No. | Ingredients | % w/w |
|---|---|---|
| 1 | Inulin | 94.34 |
| 2 | Betaine | 1.80 |
| 3 | Omega-3 fatty acid | 2.70 |
| 4 | SCFA (Sodium Propionate) | 0.90 |
| 5 | Flavouring agent (Vanilla) | 0.09 |
| 6 | Sweetening agent (Sucralose) | 0.18 |
| | Final Wt. of Powder | 100 |

Example 15

| Sr. No. | Ingredients | % w/w |
|---|---|---|
| 1 | Inulin Sulphate | 93.75 |
| 2 | Glycine Betaine | 5.09 |
| 3 | Omega-3 fatty acid | 0.89 |
| 4 | Flavouring agent (Mixed fruit) | 0.09 |
| 5 | Sweetening agent (Aspartame) | 0.18 |
| | Final Wt. of Powder | 100 |

Example 16

| Sr. No. | Ingredients | % w/w |
|---|---|---|
| 1 | Inulin | 93.94 |
| 2 | Betaine | 1.71 |
| 3 | SCFA (Sodium Butyrate) | 1.71 |
| 4 | Resistant Starch | 2.56 |
| 5 | Flavouring agent (Orange) | 0.09 |
| | Final Wt. of Powder | 100 |

Example 17

| Sr. No. | Ingredients | % w/w |
|---|---|---|
| 1 | Inulin | 96.40 |
| 2 | Betaine | 2.51 |
| 3 | Resistant Starch | 0.84 |
| 4 | Flavouring agent (Banana) | 0.08 |
| 5 | Sweetening agent (Sorbitol) | 0.17 |
| | Final Wt. of Powder | 100 |

Example 18

| Sr. No. | Ingredients | % w/w |
|---|---|---|
| 1 | Oligofructose enriched Inulin | 91.44 |
| 2 | Glycine Betaine | 7.48 |
| 3 | SCFA (Sodium Butyrate) | 0.83 |
| 4 | Flavouring agent (Mixed fruit) | 0.08 |
| 5 | Sweetening agent (Xylitol) | 0.17 |
| | Final Wt. of Powder | 100 |

Example 19

| Sr. No. | Ingredients | % w/w |
|---|---|---|
| 1 | Inulin | 94.00 |
| 2 | Betaine | 1.00 |
| 3 | Resistant Starch | 5.00 |
| | Final Wt. of Powder | 100 |

Example 20

| Sr. No. | Ingredients | % w/w |
|---|---|---|
| 1 | Inulin | 91.96 |
| 2 | Betaine | 2.68 |
| 3 | Omega-3 fatty acid | 5.36 |
| | Final Wt. of Powder | 100 |

Example 21

| Sr. No. | Ingredients | % w/w |
|---|---|---|
| 1 | Inulin | 92.00 |
| 2 | Betaine | 3.20 |
| 3 | SCFA (Sodium Butyrate) | 4.80 |
| | Final Wt. of Powder | 100 |

Example 22

| Sr. No. | Ingredients | % w/w |
|---|---|---|
| 1 | Inulin Propionate Ester | 92.88 |
| 2 | Glycine Betaine | 2.06 |
| 3 | SCFA (Sodium Propionate) | 5.06 |
| | Final Wt. of Powder | 100 |

Example 23

| Sr. No. | Ingredients | % w/w |
|---|---|---|
| 1 | Inulin Propionate Ester | 94.74 |
| 2 | Betaine Hydrochloride | 1.58 |
| 3 | MCC pH 101 | 1.05 |
| 4 | Croscarmellose Sodium | 1.05 |

-continued

| Sr. No. | Ingredients | % w/w |
|---|---|---|
| 5 | Magnesium Stearate | 0.53 |
| 6 | Talc | 0.42 |
| 7 | Zinc Stearate | 0.32 |
| 8 | Colloidal silicon dioxide | 0.32 |
| | Final Wt. of Capsule | 100.00 |

Example 24

| Sr. No. | Ingredients | % w/w |
|---|---|---|
| | Intragranular Ingredients | |
| 1 | Inulin Sulphate | 90.36 |
| 2 | Betaine Anhydrous | 2.26 |
| 3 | MCC pH 101 | 1.66 |
| 4 | Croscarmellose Sodium | 1.51 |
| | Binder Solution | |
| 5 | Hypromellose | 1.51 |
| 6 | Polysorbate 80 | 1.51 |
| 7 | IPA | QS |
| 8 | Water | QS |
| | Extragranular Ingredients | |
| 9 | Magnesium Stearate | 0.45 |
| 10 | Talc | 0.15 |
| 11 | Zinc Stearate | 0.30 |
| 12 | Colloidal silicon dioxide | 0.30 |
| | Final Wt. of Capsule | 100.00 |

Example 25

| Sr. No. | Ingredients | % w/w |
|---|---|---|
| | Intragranular Ingredients | |
| 1 | Inulin Propionate Ester | 94.74 |
| 2 | Glycine Betaine | 0.74 |
| 4 | Lactose monohydrate | 1.05 |
| 5 | Sodium starch glycolate | 1.05 |
| | Binder Solution | |
| 6 | PVP K-30 | 0.53 |
| 7 | Polysorbate 80 | 1.05 |
| 9 | IPA | QS |
| 10 | Water | QS |
| | Extragranular Ingredients | |
| 11 | Sodium starch glycolate | 0.53 |
| 12 | Magnesium Stearate | 0.16 |
| 13 | Colloidal silicon dioxide | 0.16 |
| | Final Wt. of Tablet | 100 |

Example 26

| Sr. No. | Ingredients | % w/w |
|---|---|---|
| | Dry Mixing | |
| 1 | Oligofructose enriched Inulin | 92.78 |
| 2 | Betaine Hydrochloride | 1.03 |
| 3 | MCC pH 102 | 1.24 |
| 4 | Crospovidone | 0.62 |
| 5 | Croscarmellose sodium | 0.41 |
| 6 | Magnesium Stearate | 0.52 |
| 7 | Colloidal silicon dioxide | 0.31 |
| | Seal coating Ingredients | |
| 8 | InstaMoistshield | 0.62 |
| 9 | Isopropyl alcohol | QS |
| 10 | Methylene dichloride | QS |
| | Enteric coating Ingredients | |
| 11 | Instacoat EN HPMC P | 2.47 |
| 12 | Isopropyl alcohol | QS |
| 13 | Methylene dichloride | QS |
| | Final Wt. of Enteric coated tablet | 100.00 |

Example 27

| Sr. No. | Ingredients | % w/w |
|---|---|---|
| 1 | Inulin Sulphate | 93.46 |
| 2 | Betaine Anhydrous | 1.87 |
| 3 | Flavouring agent (Vanilla) | 0.37 |
| 4 | Sweetening agent (Sucralose) | 0.09 |
| 5 | Glycerol | 3.74 |
| 6 | Preservative (Methylparaben) | 0.37 |
| 7 | Anti-oxidant (Lecithin) | 0.09 |
| 8 | Water | Qs |
| | Final Wt. of Solution | 100 |

Example 28

| Sr. No. | Ingredients | % w/w |
|---|---|---|
| 1 | Oligofructose enriched Inulin | 95.24 |
| 2 | Glycine Betaine | 2.86 |
| 3 | Flavouring agent (Mixed fruit) | 0.19 |
| 4 | Sweetening agent (Aspartame) | 0.05 |
| 5 | Glycerol | 1.43 |
| 6 | Preservative (Ethylparaben) | 0.19 |
| 7 | Anti-oxidant (Fumaric acid) | 0.05 |
| 8 | Water | Qs |
| | Final Wt. of Solution | 100 |

Example 29: Stability Data of Example 2

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 101.50% | 97.90% | 98.10% | 98.20% | 97.60% |
| 2.2 | Betaine | 90%-110% | 102.00% | 99.80% | 100.20% | 98.50% | 97.20% |

Example 30: Stability Data of Example 3

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 99.60% | 98.90% | 98.60% | 98.60% | 97.90% |
| 2.2 | Betaine | 90%-110% | 102.40% | 100.20% | 99.70% | 99.30% | 98.70% |

Example 31: Stability Data of Example 4

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 98.70% | 99.10% | 98.00% | 97.60% | 97.90% |
| 2.2 | Betaine | 90%-110% | 99.40% | 97.90% | 99.70% | 97.20% | 98.20% |

Example 32: Stability Data of Example 6

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 99.80% | 98.30% | 97.40% | 97.20% | 98.20% |
| 2.2 | Betaine | 90%-110% | 97.50% | 98.50% | 97.40% | 98.10% | 97.50% |

Example 33: Stability Data of Example 8

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 98.30% | 97.60% | 98.20% | 97.20% | 96.20% |
| 2.2 | Betaine | 90%-110% | 99.10% | 98.90% | 97.40% | 98.10% | 97.30% |
| 2.3 | Omega-3 Fatty acid | 90%-110% | 97.30% | 96.80% | 97.40% | 96.80% | 96.70% |

Example 34: Stability Data of Example 10

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 97.90% | 97.20% | 98.10% | 97.30% | 96.40% |
| 2.2 | Betaine | 90%-110% | 97.20% | 98.10% | 98.20% | 97.50% | 96.80% |
| 2.3 | SCFA (Sodium Butyrate) | 90%-110% | 95.40% | 94.20% | 95.40% | 94.10% | 94.50% |

Example 35: Stability Data of Example 11

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 98.30% | 97.60% | 98.20% | 97.20% | 96.20% |
| 2.2 | Betaine | 90%-110% | 97.50% | 98.50% | 97.40% | 98.10% | 97.50% |

Example 36: Stability Data of Example 13

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 96.90% | 95.60% | 96.40% | 95.20% | 96.30% |
| 2.2 | Betaine | 90%-110% | 98.10% | 97.80% | 97.30% | 96.90% | 96.50% |
| 2.3 | Omega-3 Fatty acid | 90%-110% | 96.40% | 95.70% | 96.10% | 95.10% | 94.70% |

Example 37: Stability Data of Example 14

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 95.60% | 94.50% | 94.70% | 93.70% | 94.30% |
| 2.2 | Betaine | 90%-110% | 98.40% | 97.50% | 96.50% | 96.40% | 96.30% |
| 2.3 | Omega-3 Fatty acid | 90%-110% | 95.70% | 94.60% | 93.70% | 94.60% | 94.80% |
| 2.4 | SCFA (Sodium Propionate) | 90%-110% | 94.20% | 94.60% | 94.10% | 92.90% | 93.10% |

Example 38: Stability Data of Example 16

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 95.60% | 95.10% | 96.00% | 94.60% | 94.70% |
| 2.2 | Betaine | 90%-110% | 97.30% | 96.30% | 97.30% | 96.40% | 96.40% |
| 2.3 | SCFA (Sodium Butyrate) | 90%-110% | 95.80% | 94.60% | 94.10% | 92.90% | 92.70% |

Example 39: Stability Data of Example 17

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 97.60% | 97.10% | 97.50% | 97.30% | 97.70% |
| 2.2 | Betaine | 90%-110% | 97.30% | 96.30% | 97.30% | 96.40% | 96.20% |

Example 40: Stability Data of Example 19

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 99.60% | 98.90% | 98.60% | 98.60% | 97.90% |
| 2.2 | Betaine | 90%-110% | 97.30% | 96.30% | 97.30% | 96.40% | 96.40% |

Example 41: Stability Data of Example 20

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |
| 2 | | | | Assay | | | |
| 2.1 | Inulin | 90%-110% | 98.60% | 98.10% | 97.10% | 97.60% | 96.70% |
| 2.2 | Betaine | 90%-110% | 98.30% | 98.30% | 97.80% | 97.40% | 97.40% |
| 2.3 | Omega-3 Fatty acid | 90%-110% | 96.80% | 96.50% | 96.10% | 95.90% | 95.70% |

Example 42: Stability Data of Example 21

| | Duration of Study | | | 3 M 40° C./ | 3 M 25° C./ | 6 M 40° C./ | 6 M 25° C./ |
|---|---|---|---|---|---|---|---|
| Sr. No. | Test | Specification | Initial | 75% RH | 60% RH | 75% RH | 60% RH |
| 1 | Description | White free flowing powder | Complies | Complies | Complies | Complies | Complies |

-continued

| Sr. No. | Test | Specification | Initial | 3 M 40° C./ 75% RH | 3 M 25° C./ 60% RH | 6 M 40° C./ 75% RH | 6 M 25° C./ 60% RH |
|---|---|---|---|---|---|---|---|
| | Duration of Study | | | | | | |
| 2 | | | | Assay | | | |
| 2.1 | Inulin | 90%-110% | 97.60% | 97.10% | 98.10% | 97.90% | 97.70% |
| 2.2 | Betaine | 90%-110% | 97.50% | 97.30% | 98.10% | 97.90% | 97.20% |
| 2.3 | SCFA (Sodium Butyrate) | 90%-110% | 95.80% | 94.60% | 94.10% | 94.50% | 94.40% |

Example 43: Animal Study

The effect of the compositions of the present invention and other test and reference compositions was studied in animals. For this study, screening effect of synergistic combination or composition/formulation comprising Inulin and other active ingredients against 5/6 Nephrectomy induced chronic kidney disease (CKD) in rat was performed. The following trials were carried out:

Eighty Four (84) female rats (Wistar rats (Rattus norvegicus)) divided into 14 groups (6 per group) were maintained in animal house in a light/dark atmosphere based on a 12 hour cycle having temperature and relative humidity in the range of 19 to 25±2° C. and 30-70%, respectively. To maintain the appropriate conditions, temperature and relative humidity were recorded three times daily. All animals were acclimatized for a minimum period of five days. Animals were maintained in the test setup for minimum 30 minutes once during the acclimatization period to reduce the stress. Animals were weighed on the day of receipt and observed daily for abnormalities if any. Detailed records of acclimatization were also maintained. Rats were housed 3 per cage in clean, sterilized Polypropylene cages. During complete experiment, animals were supplied with the standard certified rat pellet feed and drinking water treated by the reverse osmosis ad libitum.

In order to evaluate the activity against chronic kidney disease, eighty four (84) rats were screened and divided into Fourteen (14) groups. For a comparative analysis, groups were divided as normal control (Group 1 (G1)), sham Control (Group 2 (G2)), disease control (Group 3 (G3)), treatment groups with individual components (Group 4 (G4), Group 5 (G5) and Group 6 (G6) as Inulin, Betaine and Resistant Starch respectively), test composition (Group 7 (G7) to Group 11 (G11) (Combination of Inulin with Betaine at different dose level), test composition Group 12 (G12) to Group 13 (G13) (Combination of Inulin, Betaine and Resistant Starch) and reference standard (Group 14 (G14)) (Activated Charcoal). Table 1 provides the details of the various groups and treatments conducted in the trial wherein G4 to G14 are treatment groups. Experiment was carried out for 3 months in two stages.

TABLE 1

| Sr. No. | Group | Group Name | No. of Animals (Female Rats) | Dose (g/kg, p.o.) |
|---|---|---|---|---|
| 1 | G1 | Normal Control | 6 | Normal Control |
| 2 | G2 | Sham Control | 6 | Sham Control |
| 3 | G3 | Disease Control | 6 | Disease Control |
| 4 | G4 | Inulin | 6 | Inulin (1.03 g/kg) |
| 5 | G5 | Betaine | 6 | Betaine (0.03 g/kg) |
| 6 | G6 | Resistant Starch | 6 | Resistant Starch (0.10 g/kg) |
| 7 | G7 | Combination of Inulin (Inulin + Betaine) (Ex. 1) | 6 | Inulin (0.88 g/kg) + Betaine (0.11 g/kg) |
| 8 | G8 | Combination of Inulin (Inulin + Betaine) (Ex. 2) | 6 | Inulin (0.93 g/kg) + Betaine (0.10 g/kg) |
| 9 | G9 | Combination of Inulin (Inulin + Betaine) (Ex. 3) | 6 | Inulin (1.03 g/kg) + Betaine (0.03 g/kg) |
| 10 | G10 | Combination of Inulin (Inulin + Betaine) (Ex. 4) | 6 | Inulin (1.03 g/kg) + Betaine (0.01 g/kg) |
| 11 | G11 | Combination of Inulin (Inulin + Betaine) (Ex. 5) | 6 | Inulin (0.93 g/kg) + Betaine (0.001 g/kg) |
| 12 | G12 | Combination of Inulin (Inulin + Betaine + Resistant Starch) (Ex. 6) | 6 | Inulin (1.03 g/kg) + Betaine (0.01 g/kg) + Resistant Starch (0.10 g/kg) |
| 13 | G13 | Combination of Inulin Inulin + Betaine + Resistant Starch (Ex. 7) | 6 | Inulin (1.03 g/kg) + Betaine (0.01 g/kg) + Resistant Starch (0.05 g/kg) |
| 14 | G14 | Reference Standard | 6 | Activated Charcoal (0.62 g/kg) |

Treatment Protocol

The animals under consideration were examined for a study period of 13 weeks and two-stage surgical procedure for kidney ligation and removal were performed.

Stage one: A ventral midline incision into the abdomen was made to expose the animal's left kidney and the organ was freed from the surrounding tissue. A piece of suture was placed and ligated around each pole of the kidney at its one-third position. The one-third kidney on each pole was excised beyond the ligatures and the abdominal incision was closed.

Stage two: This procedure was performed 7 days after stage one. The animals were placed in ventral recumbency and an incision was made parallel to the midline. The abdominal cavity was entered, and the right kidney was made free from the surrounding tissue. The kidney was gently pulled out from the incision and the adrenal gland was freed and replaced into the abdominal cavity. The renal blood vessels and the ureter were ligated or cauterized. The kidney was then removed by transecting the vessels and ureter just distal to the ligature or cauterized section. The skin incision was closed with wound clips.

Treatment: All treatment groups were treated on daily basis for 13 weeks after stage two of surgery. Blood collection and biochemistry analysis were done after completion of the treatment of all treated groups at the end of 13th week treatment.

Table 2 represents the summary of the results obtained by effect of administering of 'Test Composition/Formulation' against 5/6 Nephrectomy induced Chronic Kidney Disease in rat.

TABLE 2

| | | IS | | PCS | |
|---|---|---|---|---|---|
| Group | Group Name | Mean (mg/L) | % Decreased | Mean (mg/L) | % Decreased |
| G1 | Normal Control | 3.26 | 0 | 0.15 | 0 |
| G2 | Sham Control | 3.16 | 0 | 0.22 | 0 |
| G3 | Disease Control | 7.33 | 0 | 1.13 | 0 |
| G4 | Inulin | 5.55 | 24.29 | 0.84 | 25.66 |
| G5 | Betaine | 7.01 | 4.37 | 1.09 | 3.54 |
| G6 | RS | 6.5 | 11.33 | 1.01 | 10.62 |
| G7 | I + B (Ex 1) | 4.31 | 41.20 | 0.65 | 42.48 |
| G8 | I + B (Ex 2) | 3.83 | 47.75 | 0.55 | 51.33 |
| G9 | I + B (Ex 3) | 3.72 | 49.25 | 0.51 | 54.87 |
| G10 | I + B (Ex 4) | 3.78 | 48.43 | 0.52 | 53.98 |
| G11 | I + B (Ex 5) | 4.21 | 42.57 | 0.63 | 44.25 |
| G12 | I + B + RS (Ex 6) | 3.69 | 49.66 | 0.50 | 55.75 |
| G13 | I + B + RS (Ex 7) | 3.67 | 49.93 | 0.49 | 56.64 |
| G14 | Activated Charcoal | 3.86 | 47.34 | 0.56 | 50.44 |

* All above values are in mean

Interpretation and Inference

As there are many reasons behind the kidney diseases as discussed above in the specification, there are important Biochemical parameters such as Indoxyl Sulphate (IS) and P-Cresyl Sulphate (PCS) to diagnose CKD wherein level of these parameters increases significantly.

In the above study, the % decrease in IS and PCS blood level was studied for the various test compositions. For the normal control group (G1) and the sham control group (G2), no significant difference in the IS and PCS blood level was observed. As compared to G1 and G2, in the disease control group (G3), significant increase in the IS and PCS blood level was observed. This eventually confirms that the disease model was successfully induced with condition of CKD in all the animals.

Analysis of Important Biomarkers

As evident from the data summarized in the Table 2, the following observation can be made:

Inulin (G4), when administered alone, showed significant decrease in IS and PCS blood level, i.e., 24.29% and 25.66% respectively. But Betaine (G5), when administered alone, did not show any significant effect. The decrease in IS and PCS blood level was only 4.37% and 3.54% respectively for Betaine, indicating that Betaine alone does not have any role in reduction of IS and PCS blood level. For Resistant Starch (G6) also, when administered alone, there was no clinically significant reduction in the IS and PCS blood level. The reduction in IS and PCS blood level with Resistant Starch was 11.33% and 10.62% respectively. The individual administration of Inulin, Betaine and Resistant Starch shows that only Inulin can be considered to have some significant effect on the reduction of IS and PCS blood levels.

As compared to the above, when Inulin and Betaine were administered together or in combination, (G7 to G11), showed a significant reduction in IS and PCS blood levels, ranging from 41.20% to 49.25% and 42.48% to 54.87% respectively. This shows that, while Betaine alone does not have any role in controlling IS and PCS levels, but it synergistically enhances the effect of Inulin, i.e., the combination of Inulin and Betaine provided a synergistic effect in decreasing the IS and PCS blood levels. It can be further observed that, when the combination of Inulin and Betaine was administered in judiciously selected amount ranging from 90 to 99% by wt. of the composition for Inulin and from 0.5 to 10% by wt. of the composition for Betaine, there was significant synergistic effect as observed for G8, G9 and G10.

It can be further observed that, when Resistant Starch was added to the combination of Inulin and Betaine (G12 and G13), there was further decrease in the IS and PCS blood levels showing that even Resistant Starch further aided in the synergistic effect of the composition of the present invention. The effect obtained by the combination of Inulin and Betaine is comparable and/or better than the reference standard group (G14), especially the combination of Inulin and Betaine when combined in judiciously selected amounts showed higher effect as compared to reference standard—Activated Charcoal. Similarly, the combination of Inulin, Betaine and Resistant Starch showed higher effect as compared to reference standard—Activated Charcoal.

Based on the above obtained result, it can be concluded that the test composition/formulation of the present invention, i.e., combination of Inulin and Betaine or combination of Inulin, Betaine and Resistant Starch have synergistic activity over the individual components and also the treatment were effective to control the kidney functions by way of reducing protein bound uremic toxins such as Indoxyl Sulphate (IS) and P-Cresyl Sulphate (PCS).

Regarding Mortality

There was no mortality observed in case of all treatment groups (G4-G14) during treatment period 13 weeks.

CONCLUSION

Based on the experimental study conducted on animals, it can be concluded that the test composition/formulation of the present invention, i.e., combination of Inulin and Betaine and combination of Inulin, Betaine with additional active ingredient(s) such as Resistant Starch was found to be more effective on reducing protein bound uremic toxins in CKD and has a synergistic effect (G7-G13 especially G8-10 and G12-13) when compared with the individual active ingredients. Especially, the effect obtained by the synergistic combination of Inulin and Betaine or Inulin, Betaine and additional active ingredient(s) such as Resistant Starch showed higher effect as compared to reference standard—Activated Charcoal.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

We claim:

1. A pharmaceutical composition comprising a combination of:

(a) Inulin or pharmaceutically acceptable salts thereof and (b) Betaine or pharmaceutically acceptable salts thereof, wherein an amount of the Inulin or pharmaceutically acceptable salts thereof ranges from 90 to 99% by wt. of the composition.

2. The pharmaceutical composition as claimed in claim 1, wherein an amount of the Betaine or pharmaceutically acceptable salts thereof ranges from 0.5 to 10% by wt. of the composition.

3. The pharmaceutical composition as claimed in claim 1, wherein the composition further comprises additional active ingredients selected from Resistant Starch, Short chain fatty acid(s) or pharmaceutically acceptable salts thereof, Omega-3 fatty acid, or a combination thereof.

4. The pharmaceutical composition as claimed in claim 3, wherein an amount of the Resistant Starch ranges from 0.8 to 9% by wt. of the composition.

5. The pharmaceutical composition as claimed in claim 3, wherein an amount of the Omega-3 fatty acid ranges from 0.89 to 9% by wt. of the composition.

6. The pharmaceutical composition as claimed in claim 3, wherein an amount of the Short chain fatty acid(s) or pharmaceutically acceptable salts thereof ranges from 0.8 to 8.2% by wt. of the composition.

7. The pharmaceutical composition as claimed in claim 1, further comprising pharmaceutically acceptable excipients.

8. The pharmaceutical composition as claimed in claim 7, wherein the pharmaceutically acceptable excipients are selected from a diluent, disintegrant, binder, glidant, lubricant, surfactant, carrier, antioxidant, preservative, flavouring agent, sweetening agent, solvent, coating agent, solubilizing agent or any combination thereof.

9. The pharmaceutical composition as claimed in claim 1, wherein the composition is in the form of a tablet, capsule, sachet, pill, hard capsule filled with liquid or solid, soft capsule, powder, granule, suspension, solution, modified release formulation, emulsion or syrup.

10. The pharmaceutical composition as claimed claim 1, wherein the composition is used for reducing protein bound uremic toxins in chronic kidney disease (CKD).

11. A pharmaceutical composition comprising a combination of:

(a) Inulin or pharmaceutically acceptable salts thereof and (b) Betaine or pharmaceutically acceptable salts thereof, wherein an amount of Betaine or pharmaceutically acceptable salts thereof ranges from 0.5 to 10% by wt. of the composition.

12. The pharmaceutical composition as claimed in claim 11, wherein the composition further comprises additional active ingredients selected from Resistant Starch, Short chain fatty acid(s) or pharmaceutically acceptable salts thereof, Omega-3 fatty acid, or a combination thereof.

13. The pharmaceutical composition as claimed in claim 12, wherein an amount of the Resistant Starch ranges from 0.8 to 9% by wt. of the composition.

14. The pharmaceutical composition as claimed in claim 12, wherein an amount of the Omega-3 fatty acid ranges from 0.89 to 9% by wt. of the composition.

15. The pharmaceutical composition as claimed in claim 12, wherein an amount of the Short chain fatty acid(s) or pharmaceutically acceptable salts thereof ranges from 0.8 to 8.2% by wt. of the composition.

16. The pharmaceutical composition as claimed in claim 11, further comprising pharmaceutically acceptable excipients.

17. The pharmaceutical composition as claimed in claim 16, wherein the pharmaceutically acceptable excipients are selected from diluent, disintegrant, binder, glidant, lubricant, surfactant, carrier, antioxidant, preservative, flavouring agent, sweetening agent, solvent, coating agent, solubilizing agent or any combination thereof.

18. The pharmaceutical composition as claimed in claim 11, wherein the composition is in the form of a tablet, capsule, sachet, pill, hard capsule filled with liquid or solid, soft capsule, powder, granule, suspension, solution, modified release formulation, emulsion or syrup.

19. The pharmaceutical composition as claimed claim 11, wherein the composition is used for reducing protein bound uremic toxins in chronic kidney disease (CKD).

* * * * *